United States Patent
Watson et al.

(10) Patent No.: US 11,968,458 B2
(45) Date of Patent: *Apr. 23, 2024

(54) SYSTEM AND METHOD FOR EXTRACTING MULTIPLE FEEDS FROM A ROLLING-SHUTTER SENSOR

(71) Applicant: INTUITIVE SURGICAL OPERATIONS, INC., Sunnyvale, CA (US)

(72) Inventors: Jason Paul Watson, San Jose, CA (US); Ian E. McDowall, Woodside, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/301,143

(22) Filed: Apr. 14, 2023

(65) Prior Publication Data

US 2023/0328387 A1 Oct. 12, 2023

Related U.S. Application Data

(63) Continuation of application No. 17/480,549, filed on Sep. 21, 2021, now Pat. No. 11,647,295, which is a
(Continued)

(51) Int. Cl.
*G06V 10/141* (2022.01)
*A61B 1/05* (2006.01)
(Continued)

(52) U.S. Cl.
CPC ............ *H04N 23/72* (2023.01); *A61B 1/05* (2013.01); *A61B 1/0653* (2013.01); *G06T 7/521* (2017.01);
(Continued)

(58) Field of Classification Search
None
See application file for complete search history.

(56) References Cited

U.S. PATENT DOCUMENTS 5,309,227 A  5/1994 Inoue
6,493,608 B1  12/2002 Niemeyer
(Continued)

FOREIGN PATENT DOCUMENTS

CN  105187732 A  12/2015
EP  2899583 A2  7/2015
(Continued)

OTHER PUBLICATIONS

Chinese Patent Office, First Chinese Office Action for Application No. 201880010163.4, dated Jun. 25, 2021 with English Translation, 27 pages.
(Continued)

*Primary Examiner* — Tyler W. Sullivan
(74) *Attorney, Agent, or Firm* — Haynes & Boone, LLP.

(57) ABSTRACT

An imaging system and method includes a rolling shutter sensor that captures a plurality of images of a scene, a time-varying illumination source that illuminates the scene, and a processor that receives the plurality of images from the rolling shutter sensor and separates the plurality of images into a plurality of feeds. Each of the plurality of images is captured as a series of lines. The rolling shutter sensor and the time-varying illumination source are operated synchronously to cause a plurality of on-cadence lines of the rolling shutter sensor to receive more illumination from the time-varying illumination source than a plurality of off-cadence lines of the rolling shutter sensor. Each of the plurality of feeds has a different contribution of the time-varying illumination source to an overall illumination of the scene.

28 Claims, 7 Drawing Sheets

Related U.S. Application Data continuation of application No. 16/479,107, filed as application No. PCT/US2018/016905 on Feb. 5, 2018, now Pat. No. 11,159,735.

(60) Provisional application No. 62/455,137, filed on Feb. 6, 2017.

(51) Int. Cl.
*A61B 1/06* (2006.01)
*G06T 7/521* (2017.01)
*G06V 10/40* (2022.01)
*H04N 5/353* (2011.01)
*H04N 23/72* (2023.01)
*H04N 25/531* (2023.01)
*H04N 5/235* (2006.01)

(52) U.S. Cl.
CPC ............ *G06V 10/141* (2022.01); *G06V 10/40* (2022.01); *H04N 25/531* (2023.01); *G06T 2207/10016* (2013.01); *G06T 2207/10028* (2013.01); *G06T 2207/10064* (2013.01); *G06T 2207/10068* (2013.01); *G06T 2207/10152* (2013.01)

(56) References Cited

U.S. PATENT DOCUMENTS

| | | |
|---|---|---|
| 6,671,581 B2 | 12/2003 | Niemeyer et al. |
| 6,817,974 B2 | 11/2004 | Cooper et al. |
| 8,237,835 B1 | 8/2012 | Muller |
| 9,386,236 B2 | 7/2016 | Muller |
| 9,462,170 B2 | 10/2016 | Laroia et al. |
| 9,894,304 B1 | 2/2018 | Smith et al. |
| 10,506,914 B2 | 12/2019 | DiCarlo et al. |
| 11,159,735 B2 | 10/2021 | Watson et al. |
| 2001/0055462 A1 | 12/2001 | Seibel |
| 2003/0187319 A1 | 10/2003 | Kaneko et al. |
| 2007/0285526 A1 | 12/2007 | Mann et al. |
| 2008/0039696 A1 | 2/2008 | Kamihara |
| 2008/0239070 A1 | 10/2008 | Westwick et al. |
| 2008/0294056 A1 | 11/2008 | Boutet et al. |
| 2009/0135271 A1 | 5/2009 | Kurane |
| 2010/0128965 A1 | 5/2010 | Blair |
| 2010/0171875 A1 | 7/2010 | Yamamoto |
| 2011/0052082 A1 | 3/2011 | Parkov et al. |
| 2011/0063427 A1* | 3/2011 | Fengler ................ A61B 5/0071 348/E5.09 |
| 2011/0116694 A1 | 5/2011 | Gareau |
| 2011/0190639 A1 | 8/2011 | Peltie et al. |
| 2013/0070071 A1 | 3/2013 | Peltie et al. |
| 2013/0307951 A1 | 11/2013 | Ono |
| 2014/0125815 A1 | 5/2014 | Holz |
| 2014/0204427 A1 | 7/2014 | Nakazawa |
| 2014/0364690 A1 | 12/2014 | Seto |
| 2014/0371535 A1 | 12/2014 | Seto |
| 2016/0183780 A1 | 6/2016 | Docherty |
| 2018/0035019 A1 | 2/2018 | Back et al. |
| 2018/0199805 A1 | 7/2018 | Sakanoue et al. |
| 2022/0006938 A1 | 1/2022 | Watson et al. |

FOREIGN PATENT DOCUMENTS

| | | |
|---|---|---|
| JP | 2010213220 A | 9/2010 |
| KR | 101690887 B1 | 12/2016 |
| WO | WO-2014018936 A2 | 1/2014 |
| WO | WO-2015127328 A2 | 8/2015 |
| WO | WO-2018145030 A1 | 8/2018 |

OTHER PUBLICATIONS

Extended European Search Report for Application No. EP21217062.5, dated Mar. 17, 2022, 11 pages.
Extended European Search Report for Application No. EP18748602.2 dated Sep. 17, 2020, 10 pages.
International Preliminary Report on Patentability for Application No. PCT/US2018/016905, dated Aug. 15, 2019, 16 pages.
International Search Report and Written Opinion for International Application No. PCT/US2018/016905, Korean Intellectual Property Office, Republic of Korea, dated May 11, 2018, 20 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

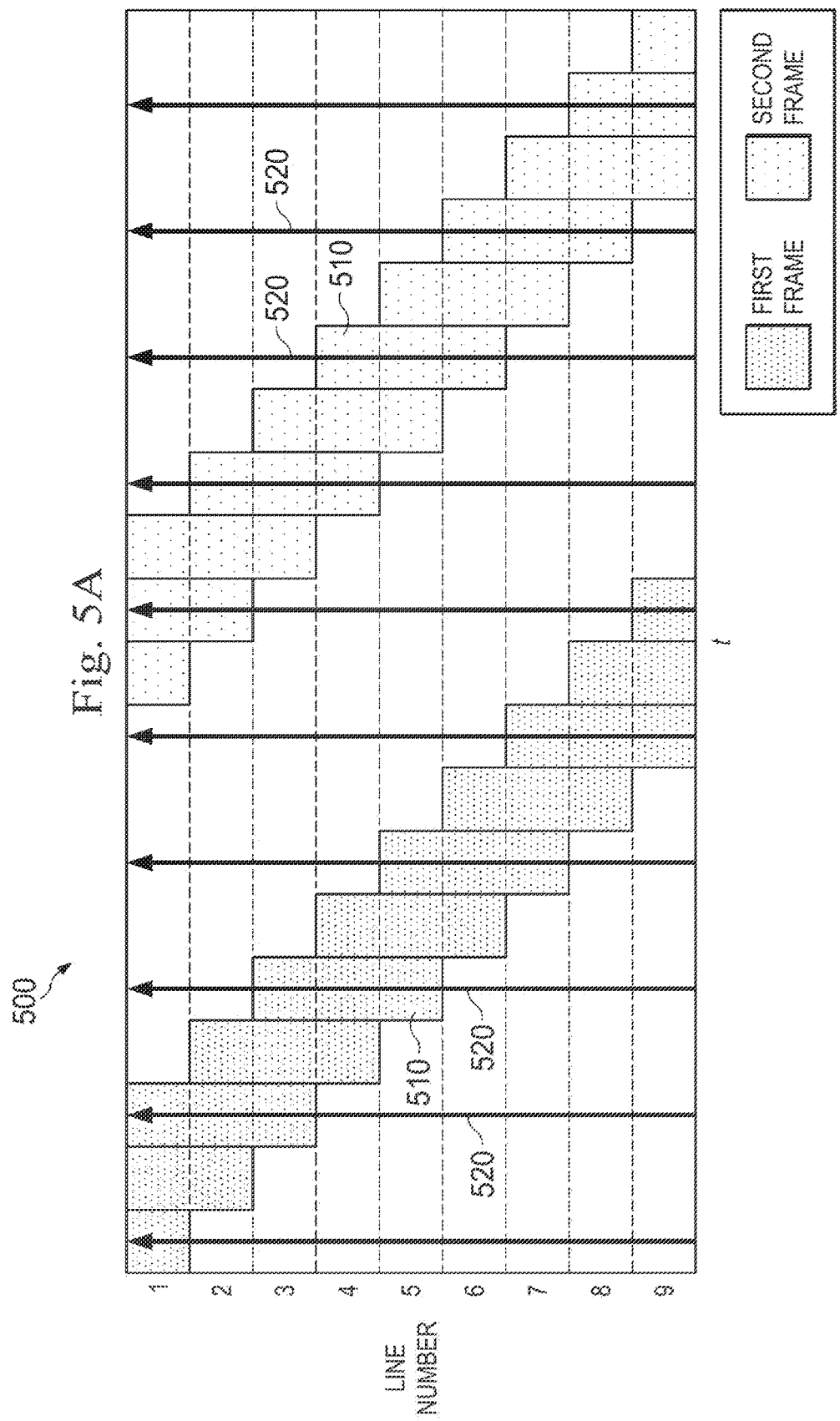

SYSTEM AND METHOD FOR EXTRACTING MULTIPLE FEEDS FROM A ROLLING-SHUTTER SENSOR

CROSS-REFERENCE TO RELATED APPLICATIONS

This patent application is a Continuation of U.S. patent application Ser. No. 17/480,549, filed Sep. 21, 2021, which is a Continuation of U.S. patent application Ser. No. 16/479,107, now U.S. Pat. No. 11,159,735, filed Jul. 18, 2019, which is the U.S. national phase of International Application No. PCT/US2018/016905, filed Feb. 5, 2018, which designated the U.S. and claims priority to and the benefit of the filing date of U.S. Provisional Patent Application 62/455,137, entitled "System and Method for Extracting Multiple Feeds from a Rolling-Shutter Sensor," filed Feb. 6, 2017, all of which are hereby incorporated by reference herein in their entireties.

TECHNICAL FIELD

The present disclosure is directed to imaging systems for conducting an image-guided procedure and more particularly to an imaging system for extracting multiple image or video feeds from a rolling-shutter sensor.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

During the performance of a medical procedure, images or videos of a surgical site may be captured under a variety of lighting conditions. For example, a surgical site may be viewed under normal or white lighting for general-purpose imaging, fluorescence lighting for fluorescence imaging, and structured lighting for optical ranging or depth estimation. Rolling-shutter sensors are one common type of image sensor used to capture images or videos of a surgical site.

Accordingly, it would be advantageous to provide an imaging system that supports extracting multiple feeds from a rolling-shutter sensor, where the multiple feeds correspond to different lighting conditions.

SUMMARY

The embodiments of the invention are best summarized by the claims that follow the description.

In some embodiments, an imaging system may include a rolling shutter sensor that captures a plurality of images of a scene, a time-varying illumination source that illuminates the scene, and a processor that receives the plurality of images from the rolling shutter sensor and separates the plurality of images into a plurality of feeds. Each of the plurality of images is captured as a series of lines. The rolling shutter sensor and the time-varying illumination source are operated synchronously to cause a plurality of on-cadence lines of the rolling shutter sensor to receive more illumination from the time-varying illumination source than a plurality of off-cadence lines of the rolling shutter sensor. Each of the plurality of feeds has a different contribution of the time-varying illumination source to an overall illumination of the scene.

In some embodiments, a method may include capturing a plurality of images of a scene using a rolling shutter sensor, illuminating the scene using a time-varying illumination source, synchronizing the rolling shutter sensor and the time-varying illumination source to cause a first subset of lines of the rolling shutter sensor to be on-cadence with the time-varying illumination source and a second subset of lines to be off-cadence, and separating the plurality of images into a plurality of feeds. Each of the plurality of feeds has a different contribution of the time-varying illumination source to an overall illumination of the scene.

In some embodiments, method may include receiving image data from a rolling shutter sensor that is operated synchronously with a time-varying illumination source, determining on-cadence lines and off-cadence lines from the received image data, determining a contribution of the time-varying illumination source to an overall illumination in the image data, and generating a plurality of feeds with different contributions of the time-varying illumination source to the overall illumination.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 5A-D are a sequence of simplified diagrams that illustrate the operation of an imaging system to extract multiple image or video feeds from a rolling shutter sensor according to some embodiments.

DETAILED DESCRIPTION

Figure 1:
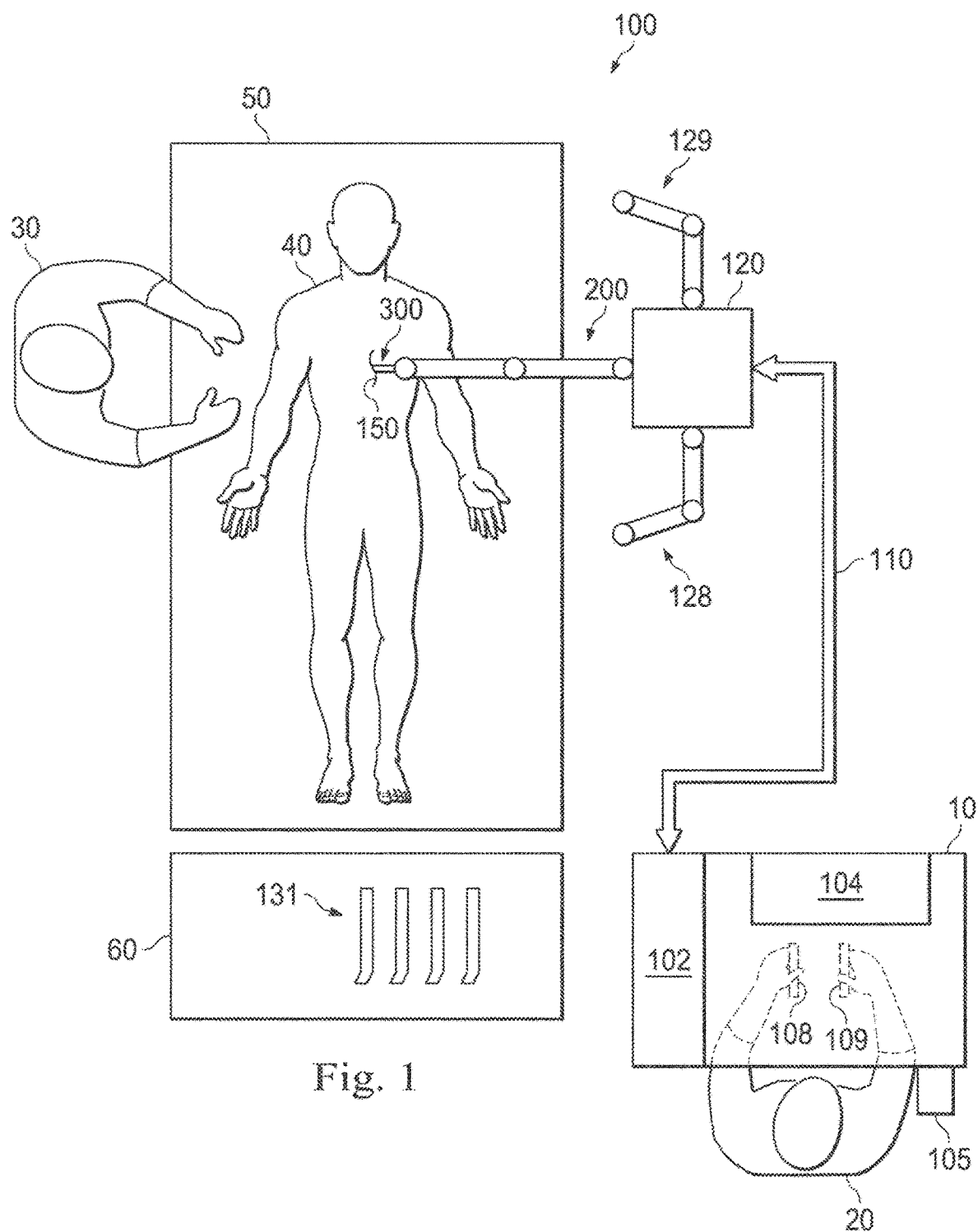
FIG. 1 is a simplified diagram of an operating room employing a surgical system with a bundled unit of medical devices according to some embodiments.

FIG. 1 illustrates, as an example, a top view of an operating room in which a surgical system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

The surgical system 100 includes at least one arm 200 and any number of additional, optional arms 128 and/or 129. Thus, surgical system 100 may be a multi-arm system and/or a single arm system, such as a single port system. One or more of arms 128, 129, and 200 may be mounted on a patient side cart 120. While system 100 is depicted as including a plurality of arms 128, 129, and 200 mounted to a common patient side cart 120 for exemplary purposes, one or more arms may additionally or alternately be provided on separate carts.

In some embodiments, arms 128, 129, and/or 200 may each support a single medical device and/or a plurality of medical devices, such as a bundled unit 300 of medical devices. In the present example, the bundled unit 300 is inserted through a single entry port 150 into the Patient 40. Although the entry port 150 is a minimally invasive incision in the performance of other medical procedures, it may instead be a natural body orifice. The bundled unit 300 is held and manipulated by the arm 200. Only the arm 200 is used in the present example. Arms 128 and 129 are swung out of the way during the performance of the present medical procedure, because they are not being used.

The console 10 includes a monitor 104 for displaying an image (e.g., a 2-D or 3-D image) of a surgical site to the Surgeon 20, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
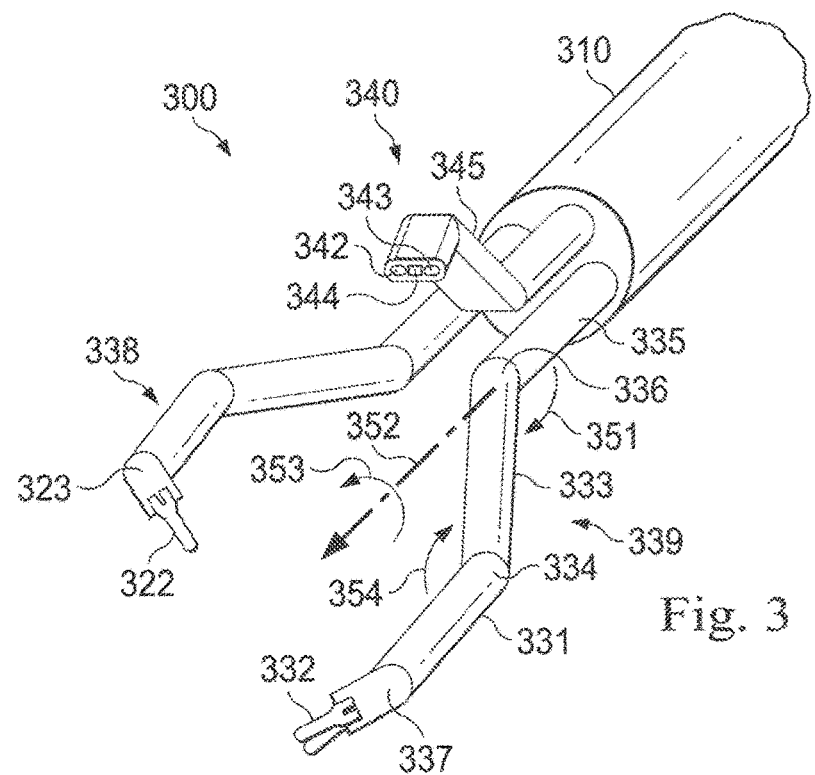
FIG. 3 is a simplified diagram of a distal end of a bundled unit of medical devices according to some embodiments.

As shown in FIG. 3, the bundled unit 300 may include two surgical instruments or tools 338, 339 and an image capturing device 340. Each of the surgical tools 338, 339 is associated with one of the control devices 108, 109. The Surgeon performs a medical procedure by manipulating the control devices 108, 109 so that the processor 102 causes corresponding movement of their respectively associated surgical tools 338, 339, while the Surgeon views the surgical site in 3-D on the console monitor 104 as it is captured by the image capturing device 140.

Control devices 108, 109 may be provided with at least the same degrees of freedom as their associated tools 338, 339 to provide the Surgeon with telepresence, or the perception that the control devices 108, 109 are integral with the tools 338, 339 so that the Surgeon has a strong sense of directly controlling the tools 338, 339.

The monitor 104 may be positioned near the Surgeon's hands so that it will display a projected image that is oriented so that the Surgeon feels that he or she is actually looking directly down onto the operating site. To that end, images of the tools 338, 339 preferably appear to be located substantially where the Surgeon's hands are located.

In addition, the real-time image may be projected into a perspective image such that the Surgeon can manipulate the end effectors 322, 332 of the tools 338, 339 through their corresponding control devices 108, 109 as if viewing the workspace in substantially true presence. By true presence, it is meant that the presentation of an image is a true perspective image simulating the viewpoint of an operator that is physically manipulating the tools 338, 339. Thus, the processor 102 transforms the coordinates of the tools 338, 339 to a perceived position so that the perspective image is the image that one would see if the image capturing device 140 was located directly behind the tools 338, 339.

The processor 102 performs various functions in the system 100. One important function that it performs is to translate and transfer the mechanical motion of control devices 108, 109 to arm 200 through control signals over bus 110 so that the Surgeon can effectively manipulate the tools 338, 339.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system such as in printed circuit boards installed in the patient side cart 120 and/or the arms 128, 129, 200, as well as, or alternatively to, the console 10.

For additional details on the construction and operation of various aspects of a surgical system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
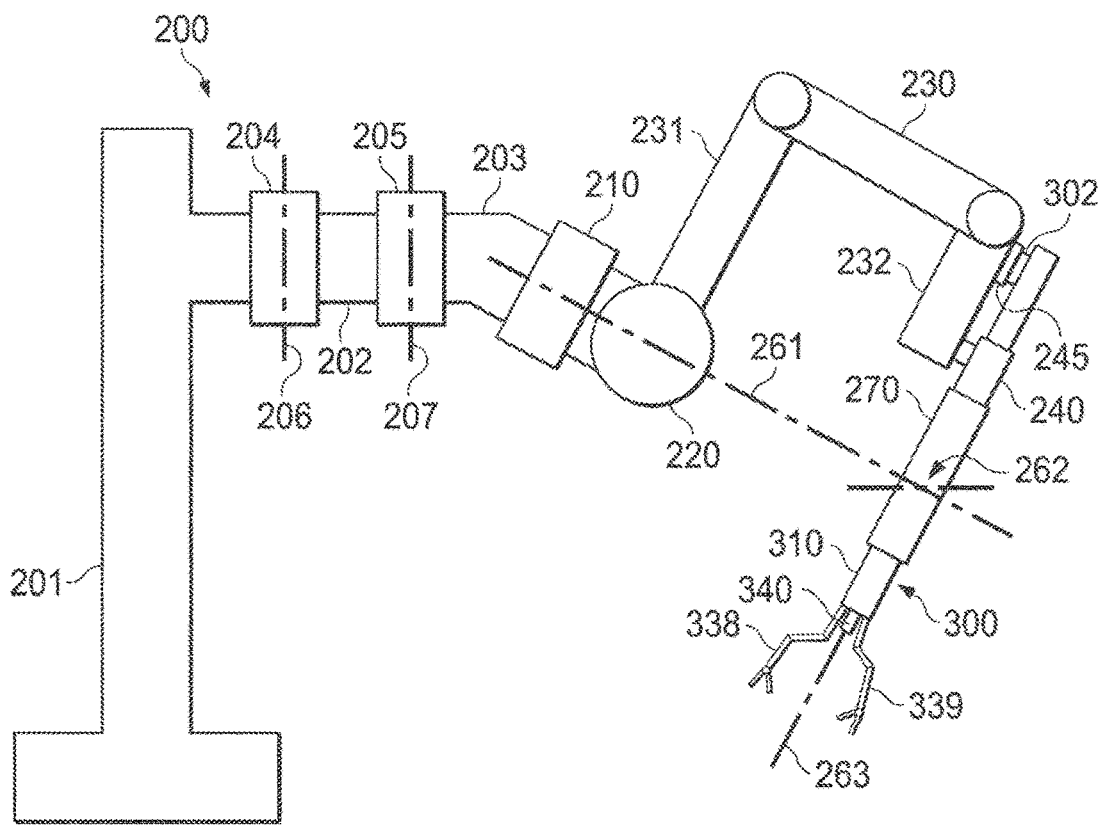
FIG. 2 is a simplified diagram of a teleoperational arm assembly holding a bundled unit of medical devices according to some embodiments.

FIG. 2 illustrates, as an example, a simplified side view (not necessarily in proportion or complete) of the arm 200 which is holding the bundled unit 300 of medical devices. A tool guide 270 is inserted through the minimally invasive incision 150 in the Patient and is coupled to arm 200 by a guide holder 240. The bundled unit 300 may then be inserted into the Patient through the tool guide 270. The arm 200 is mechanically supported by a base 201 of the patient side cart 120.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other arms in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The arm 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. An interface 302 comprises mating parts on the carriage 245 and the proximal end of the bundled unit 300 such as motor driven gears that actuate movement of the surgical tools 338, 339 and image capturing unit 340 through conventional joints, cable and pulley systems.

The arm section 230 is configured so that sections 231, 232 are always parallel to each other as the pitch joint 220 is rotated by its motor. As a consequence, the bundled unit 300 may be controllably moved by driving the yaw and pitch motors so as to pivot about the pivot point 262, which is generally located through manual positioning of the setup joints 204, 205 so as to be at the point of entry into the Patient. In addition, the bundled unit 300 is coupled to a carriage 245 on the arm section 230 which in turn is coupled to a linear drive mechanism to extend or retract the bundled unit 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the bundled unit 300 may be controlled through user (e.g., Surgeon or operator) manipulation of its associated control device.

FIG. 3 illustrates, as an example, a perspective view of a distal end of the bundled unit 300. The bundled unit 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the bundled unit 300. Replacement of one or both of the surgical tools 338, 339 during or in preparation for performing a medical procedure may then be accomplished by the Assistant removing the tool that is no longer needed from its lumen and replacing it with a substitute tool 131 from a tray 60 by inserting the substitute tool 131 in the vacated lumen. Alternatively, if unused lumens are available, an additional tool may be inserted through one of those available lumens without removing any other tools already in place.

The image capturing device 340 preferably includes a stereoscopic pair of cameras 342, 343 (and/or a single binocular camera) for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the bundled unit 300 for "seeing" into anatomic structures for surgical or diagnostic purposes.

In some embodiments, an overtube 310 is also included in the bundled unit 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the bundled unit 300 may conform to the shapes of body lumens as it moves therethrough to a surgical site within a patient.

The surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the single-port device 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing device 340 also has a controllably extendable, rotatable, and bendable arm 345 that facilitates at least insertion/retraction of the image capturing unit 340 along its insertion axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

Figure 4:
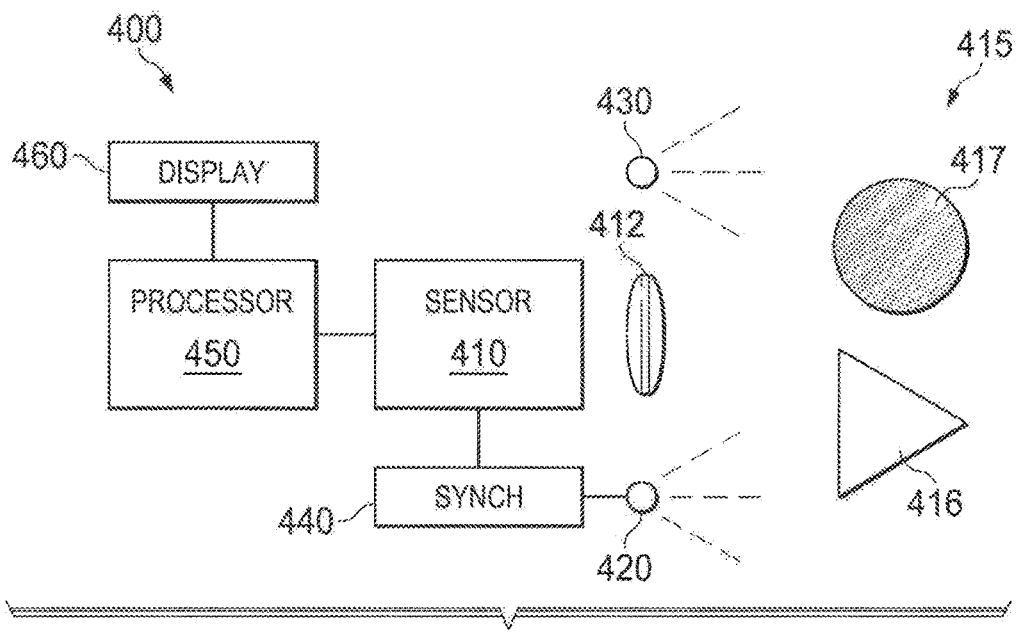
FIG. 4 is a simplified diagram of an imaging system for extracting multiple image or video feeds from a rolling shutter sensor according to some embodiments.

FIG. 4 is a simplified diagram of an imaging system 400 for extracting multiple image feeds, such a video feeds, from a rolling shutter sensor according to some embodiments. According to some embodiments consistent with FIGS. 1-3, imaging system 400 may be incorporated into a surgical system, such as surgical system 100. However, in some examples, imaging system 400 may be used for applications independent of the medical teleoperational system, such as standalone imaging applications and/or non-surgical imaging applications.

Imaging system 400 includes a rolling shutter sensor 410 that captures images or video of a scene 415. Rolling shutter sensor 410 operates by scanning across scene 415 line by line (e.g., in a horizontal or vertical sequence) to form an image or frame. Thus, a single frame is captured piecemeal, over a duration of time. By way of distinction, a global shutter sensor captures an entire image at the same point in time. In some examples, rolling shutter sensor 410 may be a complementary metal-oxide-semiconductor (CMOS) imager. CMOS imagers are available in very small sizes. For example, some CMOS imagers are small enough to be used in chip-on-tip endoscopes, where the image sensor is located at a distal end of an endoscope and inserted into the patient body. Accordingly, rolling shutter sensor 410 may be integrated into a chip-on-tip endoscope for use in surgical procedures. Consistent with such embodiments, rolling shutter sensor 410 may be disposed in an endoscope shaft, such as an 8.8 mm endoscope shaft.

Rolling shutter sensor 410 is associated with a frame rate and a line rate. The line rate is equal to the frame rate times the number of lines on the sensor. For example, rolling shutter sensor 410 may have a frame rate of 60 Hz and a sensor with 1024 vertical lines, in which case the line rate is 61.44 kHz when scanning vertically.

Imaging system 400 also includes focusing optics 412. Focusing optics 412 project one or more images of scene 415 onto rolling shutter sensor 410. Focusing optics 412 may include one or more lenses, shutters, apertures, reflectors, prisms, filters, and/or the like. In some examples, focusing optics 412 may project a single image of scene 415 onto rolling shutter sensor 410 for two-dimensional imaging. In some examples, focusing optics 412 may include binocular focusing optics to project a pair of images onto different sections of rolling shutter sensor 410. Binocular focusing optics can be used to achieve three-dimensional and/or depth imaging of scene 415. In some examples, focusing optics 412 may be mounted to the end of an endoscope shaft for chip-on-tip endoscope applications.

A time-varying illumination source 420, such as a pulsed illumination source, illuminates scene 415 while rolling shutter sensor 410 captures images of scene 415. Time-varying illumination source 420 may be a source of virtually any type of electromagnetic radiation, including narrow-band, broadband, coherent, non-coherent, isotropic, anisotropic, visible, infrared, and/or ultraviolet radiation and may be a point source and/or a distributed/diffuse source. According to some embodiments, time-varying illumination source 420 may include a solid state source of narrowband illumination, such as a solid state laser and/or a light emitting diode (LED). One or more output characteristics of time-varying illumination source 420, such as the intensity, spectral characteristics, spatial distribution, and/or the like, is modulated as a function of time. In some examples, the output characteristics may be modulated periodically as a function of time. For example, time-varying illumination source 420 may output a stream of equally spaced pulses of illumination and/or illumination with a cyclically varying intensity. In some examples, the time-varying illumination source 420 may be modulated using a time-varying electrical power supply that provides a time-varying current and/or voltage to control the output illumination, such as when time-varying illumination source 420 includes a solid state source. Alternately or additionally, time-varying illumination source 420 may be modulated using mode locking techniques, such as when time-varying illumination source 420 includes a mode-locked laser.

The modulation frequency of time-varying illumination source 420 (e.g., the pulse rate) may be significantly higher than the frame rate of rolling shutter sensor 410. In some embodiments, the modulation frequency may approach or exceed the line rate of rolling shutter sensor 410. For instance, where the frame rate is 60 Hz and the line rate is 60 kHz, a pulse rate of time-varying illumination source 420 may be 6 kHz or greater.

In some embodiments, time-varying illumination source 420 may be a fluorescence illumination source. Consistent with such embodiments, one or more objects or features in scene 415, such as an object 416, may be labeled using a fluorescent agent that absorbs and re-emits illumination from time-varying illumination source 420, such as a fluorescent dye and/or a fluorescent protein. Consequently, the fluorescence illumination source operates as an excitation source for the fluorescent agent. Other objects or features, such as an object 417, may not be labeled using the fluorescent agent.

The excitation and/or emission spectrum of the fluorescent agent may be separated from the visible light range and/or may overlap with the visible light range. An example of a fluorescent agent that with an excitation and emission spectrum that is separated from the visible light range is indocyanine green (ICG). Examples of fluorescent agents with excitation and/or emission spectra that overlap with the visible light range include fluorescein and a visible fluorescent proteins (e.g., green (GFP), yellow (YFP), blue (BFP), and/or cyan (CFP) fluorescent protein). The wavelength of the fluorescence illumination source is selected to match the excitation spectrum of the fluorescent agent, such as a wavelength in the blue or ultraviolet range when using fluorescein or GFP. For example, the fluorescence illumination source may be a narrow-band and/or a single-band illumination source, such as a laser.

In some embodiments, time-varying illumination source 420 may be a structured illumination source. That is, the output illumination may vary spatially. For example, the output illumination may be a stripe pattern, dot pattern, grid pattern, and/or the like. The illumination pattern output by the structured illumination source may be used for three dimensional positioning and/or depth estimation (e.g., optical ranging) based on deviations from the illumination pattern in the captured images. In some embodiments, the wavelength of the structured illumination source may be in the near-IR range.

A continuous illumination source 430 is optionally included to provide continuous illumination to scene 415. Unlike time-varying illumination source 420, the output illumination of continuous illumination source 430 is substantially constant over time (i.e., varying at a rate that is slower than the frame rate of rolling shutter sensor 410). In some examples, continuous illumination source 430 may output broadband and/or white light. Continuous illumination source 430 causes an image of scene 410 to be projected onto rolling shutter sensor 410 even when the output intensity of time-varying illumination source 420 is low or zero. According to some embodiments, however, continuous illumination source 430 may be omitted from imaging system 400, such as when there is sufficient ambient illumination to perform imaging without additional lighting.

Rolling shutter sensor 410 and time-varying illumination source 420 are operated synchronously such that a first predetermined subset of lines in rolling shutter sensor 410 ("on-cadence" lines) receives more illumination from time-varying illumination source 420 than a second predetermined subset of lines ("off-cadence" lines). In some examples, the off-cadence lines may receive no illumination from time-varying illumination source 420.

For example, time-varying illumination source 420 may output a stream of pulses at a pulse rate that is synchronized with the line rate of rolling shutter sensor 410. For instance, when time-varying illumination source 420 includes a mode-locked laser, the repetition rate of the mode-locked laser may be synchronized with the line rate of rolling shutter sensor 410. Due to the synchronous operation, a first (on-cadence) line of rolling shutter sensor 410 may receive more pulses of illumination from time-varying illumination source 420 than a subsequent second (off-cadence) line. In some examples, the pulse rate may further be synchronized with the frame rate of rolling shutter sensor 410. Accordingly, a particular line of rolling shutter sensor 410 may switch between on-cadence and off-cadence in alternating frames. The synchronous operation of rolling shutter sensor 410 and time-varying illumination source 420 is explained in greater detail in FIG. 5 below.

A synchronization module 440 may be used to achieve synchronization between rolling shutter sensor 410 and time-varying illumination source 420. Synchronization module 440 may include one or more clocks and/or oscillators. According to some embodiments, synchronization module 440 may include a clock that generates and sends synchronized timing signals to each of rolling shutter sensor 410 and time-varying illumination source 420. Synchronization module 440 may further include one or more delay generators and/or frequency dividers to adjust the phase and/or frequency relationships, respectively, between the synchronized timing signals. The delay generators and/or frequency dividers may be programmable and/or fixed. According to some embodiments, rolling shutter sensor 410 and/or time-varying illumination source 420 may include independent clocks that are synchronized based on a one-time initialization process at startup and/or an ongoing synchronization process that may correct for clock drift.

A processor 450 receives image data from rolling shutter sensor 410 and separates the image data into a plurality of images or video feeds. Each of the plurality of video feeds has a different contribution of time-varying illumination source 420 to the overall illumination of scene 415 (e.g. a total illumination that may also include the white light from the continuous illumination source and/or an ambient light). For example, a first video feed may be a general-purpose video feed with little or no contribution from time-varying illumination source 420. The general-purpose video feed may capture scene 415 illuminated by continuous white light and/or ambient illumination. By contrast, a second video feed may be a special-purpose video feed capturing the scene 415 illuminated by time-varying illumination source 420 in addition to the continuous white light and/or ambient light. For example, the second video feed may capture fluorescence images of scene 415 (i.e., when time-varying illumination source 420 is a fluorescence illumination source) and/or structured images of scene 415 (i.e., when time-varying illumination source 420 is a structured illumination source).

According to some embodiments, processor 450 may separate the received image data into a plurality of video feeds. For example, the received image data may be separated based on an illumination difference between the on-cadence and off-cadence lines in the received image data. For example, a particular line in the image data may switch between on-cadence and off-cadence in alternating frames. By comparing the exposure level of the off-cadence lines to the on-cadence lines, processor 450 may determine the relative contribution of time-varying illumination source 420 to the overall illumination of the corresponding region of scene 415. In various embodiments, the comparison of exposure level may be made be a pixel-level comparison. Once the relative contribution of time-varying illumination source 420 is known for each line of the image data, processor 450 may separate the image data into two or more video feeds based on the different contributions from time-varying illumination source 420. For example, processor 450 may identify, based on the difference in illumination exposure, which lines are exposed to time-varying illumination source 420. Then, based on this differential, the processor 450 may remove (e.g. filter out) the contribution of time-varying illumination source 420 from the image data for each image frame to generate the general-purpose video feed, and the processor 450 may isolate the contribution of time-varying illumination source 420 to the image data for each image frame to generate the special-purpose video feed.

Processor 450 may separate the received image data into a plurality of video feeds as described above even when the spectrum of time-varying illumination source 420 (and/or the emission spectra of fluorescent agents activated by time-varying illumination source 420) overlaps with the spectrum of other sources of illumination to scene 415. For example, rolling shutter sensor 410, time-varying illumination source 420, and continuous illumination source 420 may all operate in the visible light range. This avoids placing constraints—which may be inconvenient, costly, and/or impractical—on the spectral characteristics of time-varying illumination source 420, the types of fluorescent agents that are used for fluorescent imaging, and the filtering components, if any, that are included in focusing optics 412. Moreover, imaging system 400 may be used without spectral filters that are matched to a particular fluorescent agent, and may therefore be compatible with a variety of fluorescent agents with different excitation and/or emission spectra.

A display 460 is optionally included to show images or video corresponding to the plurality of video feeds output by processor 450. In some examples, display 460 may be a component of the surgeon's console, such as console 10. In some examples, display 460 may concurrently show two or more real-time video feeds, each of which are derived from image data captured by rolling shutter sensor 410. For example, the two or more real-time video feeds may include a general-purpose video feed (e.g., images illuminated with white and/or ambient lighting) and a special purpose video feed (e.g., images illuminated with fluorescence illumination). In some examples, display 460 may show a single video feed that combines data from the plurality of video feeds output by processor 450. For example, the combined video feed may show images in which the special purpose video feed is overlaid on the general-purpose video feed. In another example, the combined video feed may show three-dimensional images of scene 415 based on a combination of the general-purpose video feed (which may provide two-dimensional images) and the special-purpose video feed (which may provide depth information derived from structured lighting of scene 415). Consistent with some embodiments, processor 450 may determine depth information based on the structured lighting of scene 415. In some examples, the It is to be understood that FIG. 4 is merely an example, and various alternatives are possible. For example, although rolling shutter sensor 410 is described as scanning scene 415 line by line (i.e. a row or column of pixels at a time), other pixel groupings are possible. For example, the groupings may be a fraction of a line, multiple lines, a single pixel, and/or the like. Moreover, although consecutive lines in a particular frame, and a particular line in consecutive frames, are described as alternating between on-cadence and off-cadence, various other patterns are possible. The pattern of on-cadence and off-cadence lines depends generally on the relationship between the line rate of rolling shutter sensor 410 and the modulation frequency of time-varying illumination source 420. For example, when the pulse rate is one third or one fourth of the line rate every third or fourth line, respectively, may be on-cadence. In some examples, imaging system 400 may include more than one time-varying illumination source and more than one corresponding special-purpose video feed. For example, the video feeds output by processor 450 may include a general-purpose video feed and two or more special-purpose video feeds corresponding to fluorescence imaging of two or more different fluorescent agents (i.e., fluorescent agents with different excitation and/or emission spectra). Similarly, the plurality of video feeds output by processor 450 may include a general-purpose video feed, one or more special-purpose video feeds corresponding to fluorescent imaging, and one or more special-purpose video feeds corresponded to structured light imaging.

Figure 5B:
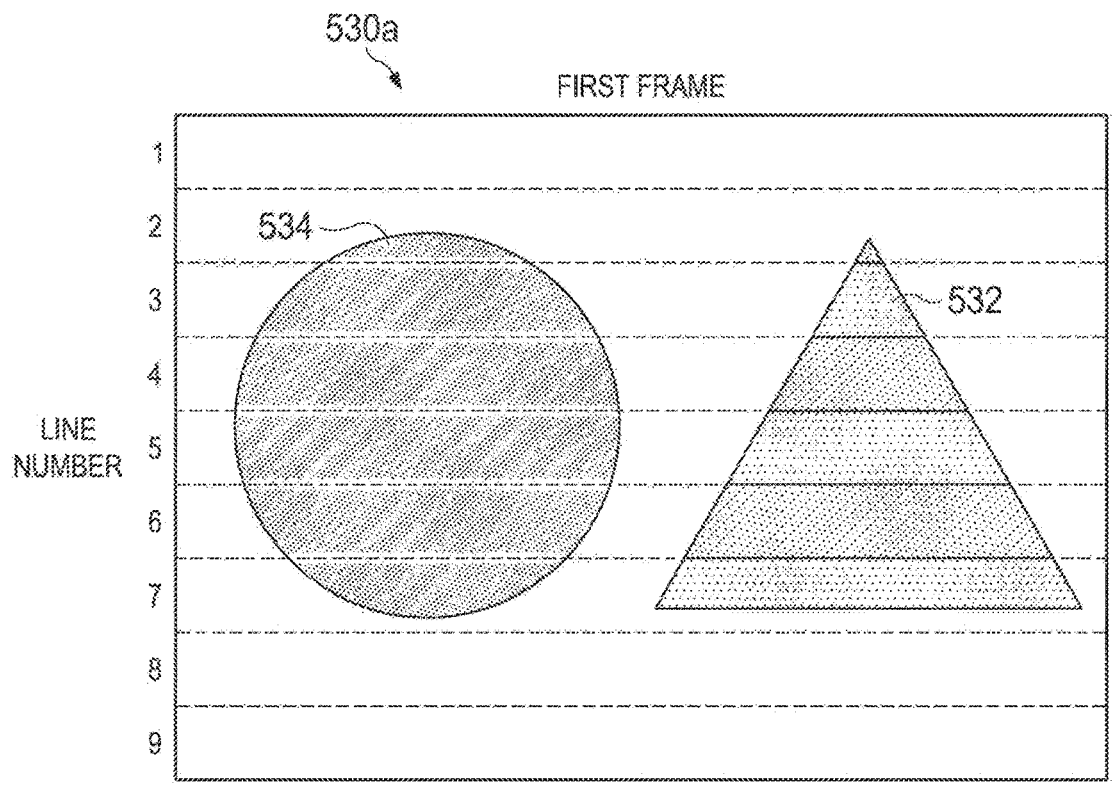

FIGS. 5A-D are a sequence of simplified diagrams that illustrate the operation of an imaging system, such as imaging system 400, to extract multiple image or video feeds from a rolling shutter sensor according to some embodiments. As depicted in FIG. 5A, a plot 500 illustrates the synchronous operation of a rolling shutter sensor, such as rolling shutter sensor 410, and a time-varying illumination source, such as time-varying illumination source 420. The rolling shutter sensor in this example has nine lines (these may be either vertical or horizontal lines) numbered one through nine. Plot 500 depicts the shutter positions (i.e., the exposed lines) of the rolling shutter sensor as a function of time during the capture of two consecutive frames.

Shaded boxes 510 represent the shutter position of the rolling shutter sensor as a function of time. In this example, the shutter has a width of three lines. That is, at any given time, three neighboring lines of rolling shutter sensor are exposed. The shutter position shifts downward one line at a time at the line rate of the rolling shutter sensor. After each line of the rolling shutter sensor has been exposed, the shutter position loops back to the top line and begins to capture the next frame. In a given frame, each line is exposed for three consecutive time slots (a time slot corresponds to the length of time that the shutter remains at a particular position, which is the inverse of the line rate).

Arrows 520 represent a plurality of pulses of illumination output by the time-varying illumination source. As demonstrated in plot 500, the time-varying illumination source and the rolling shutter sensor are synchronized. More specifically, the pulse rate of the time-varying illumination source is half the line rate of the rolling shutter sensor. Consequently, there is one pulse of illumination in every other time slot. As depicted in plot 500, the pulses occur near the middle of a given time slot, but it is to be understood that the pulses may occur at any point in a given time slot. For example, it may be desirable for the pulses to occur at the beginning of a time slot due to allow for fluorescence emission to decay before the next time slot begins. According to some embodiments, rather than a stream of pulses, the time-varying illumination source may vary cyclically over time according to some other function, such as a sinusoidal function. Consistent with such embodiments, arrows 520 may represent the peak intensity of the cyclically varying illumination source.

As depicted in plot 500, alternating lines of the rolling shutter sensor are either on-cadence or off-cadence. The on-cadence lines receive two pulses per frame, and the off-cadence lines receive one pulse per frame. For example, in the first frame, odd lines 1, 3, 5, 7, and 9 are on-cadence, and even lines 2, 4, 6, and 8 are off-cadence. In the second frame, the cadence is reversed: even lines 2, 4, 6, and 8 are on-cadence and odd lines 1, 3, 5, 7, and 9 are off-cadence.

In an alternative embodiment, the timing of the pulsed illumination may be adjusted and synchronized with the rolling shutter sensor such that the on-cadence lines receive a single pulse per frame and the off-cadence lines receive no pulses per frame.

Figure 5C:
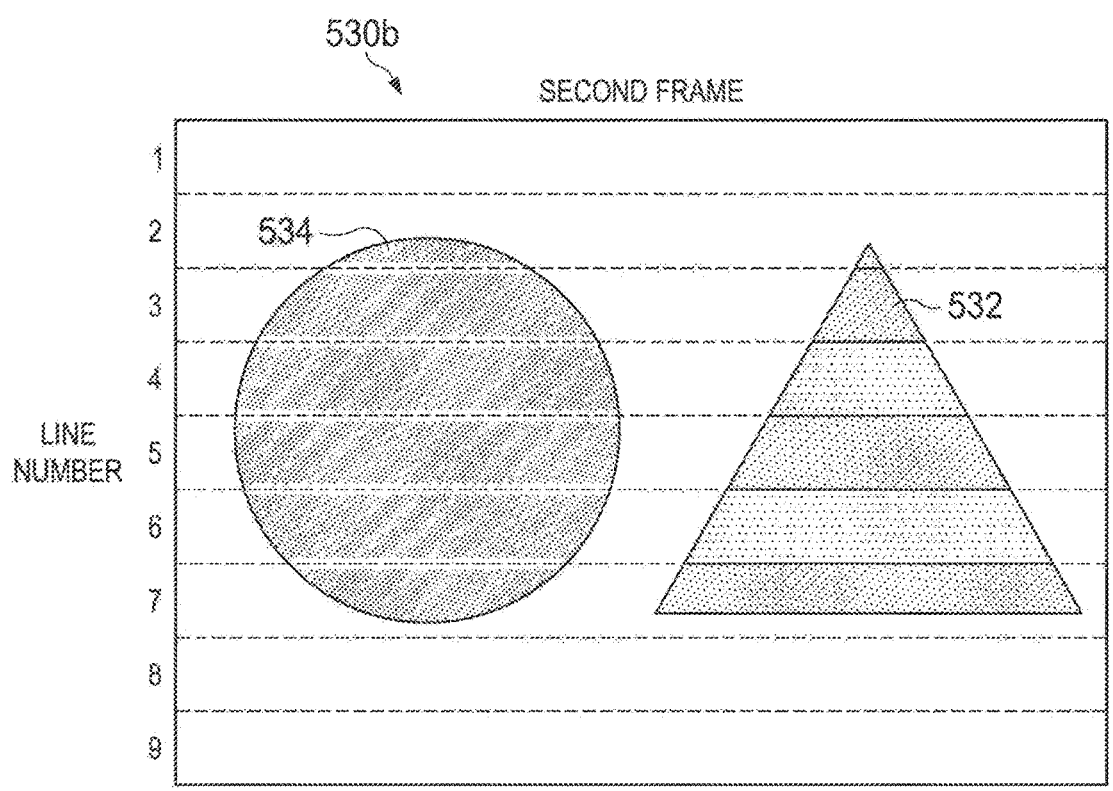

FIG. 5B depicts a first frame 530a, and FIG. 5C depicts a second frame 530b, both captured by a rolling shutter sensor during the operation illustrated in plot 500. An object 532 and an object 534 appear in each of first and second frames 530a-b. Object 532 and object 534 may generally correspond to object 416 and object 417, respectively, as depicted in FIG. 4. For example, object 532 may be labeled using a fluorescent tag, whereas object 534 may not be labeled using the fluorescent tag. Consequently, when the time-varying illumination source is a fluorescent illumination source, object 532 may emit light in response to each pulse output by the time-varying illumination source. Meanwhile, the appearance of object 534 may be constant over time, as object 534 does not emit light in response to the time-varying illumination source.

Because object 532 is responsive to the pulsed light source, lines that are on-cadence appear brighter than lines that are off-cadence, resulting in a striped appearance. In particular, odd lines 3, 5, and 7 of first frame 530a and even lines 2, 4, and 6 of second frame 530b are on-cadence (brighter) and even lines 2, 4, and 6 of first frame 530a and odd lines 3, 5, and 7 of second frame 530b are off-cadence (dimmer). By contrast, object 534 has the same brightness in all lines because it is not responsive to the pulsed light source.

Figure 5D:
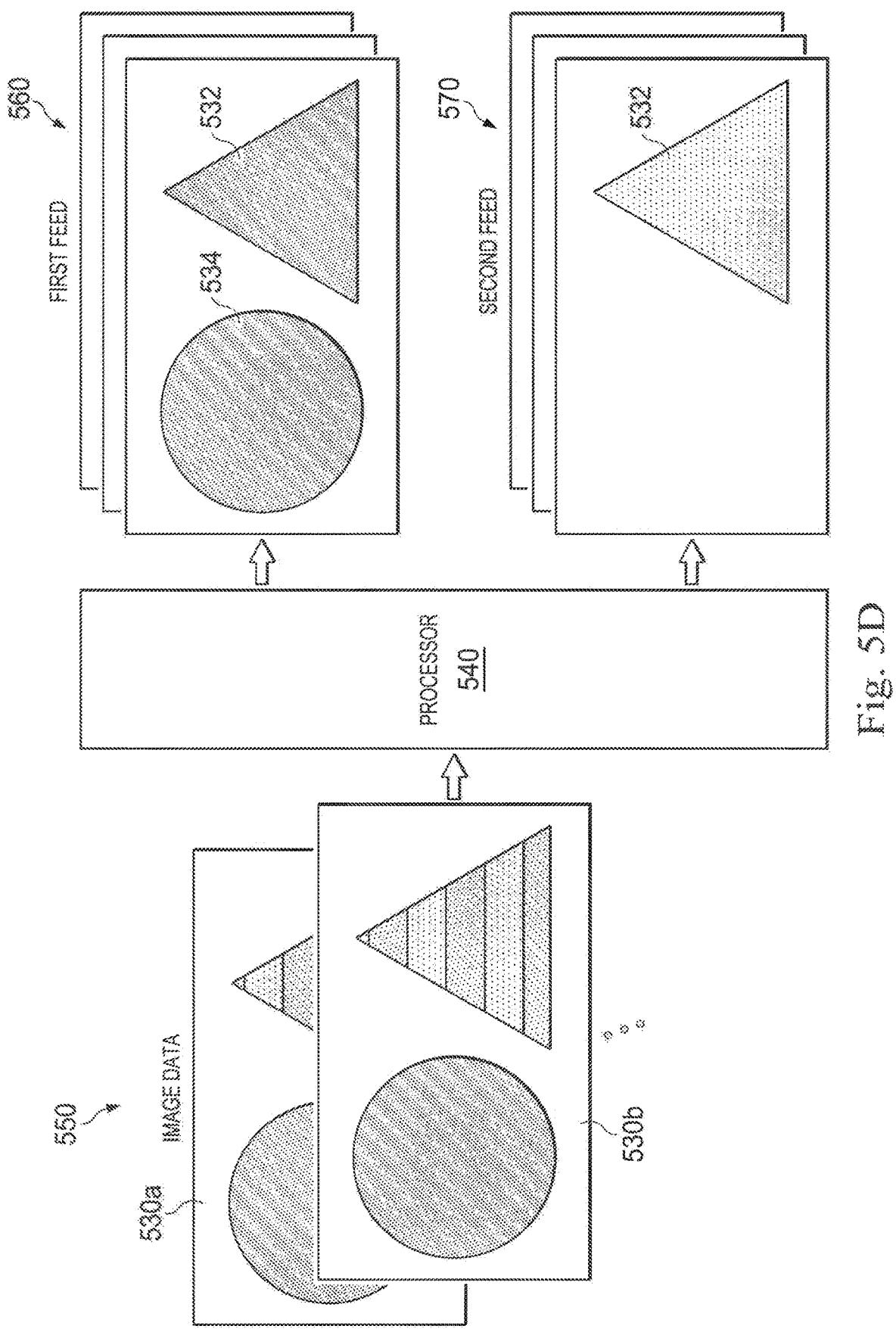

In FIG. 5D, a processor 540 receives image data 550 (which includes first and second frames 530a-b) and separates image data 550 into a first video feed 560 and a second video feed 570. According to some embodiments, processor 540 may determine the contribution of the time-varying illumination source to image data 550 based on the difference in illumination between consecutive frames, such as first and second frames 530a-b. Processor 540 then outputs first video feed 560, in which the contribution of the time-varying illumination source is removed. That is, objects 532 and 534 are shown in first video feed 560 as they appear under ambient or continuous illumination. In addition, processor 540 outputs second video feed 570, in which the contribution of the time-varying illumination source is isolated. That is, only object 532 is shown in second video feed 570, as it appears under time-varying illumination. In some examples, first video feed 560 may be a general-purpose video feed that shows objects under white light and/or ambient lighting conditions, and second video feed 570 may be a special-purpose video feed that shows objects under, for example, fluorescence and/or structured illumination.

Figure 6:
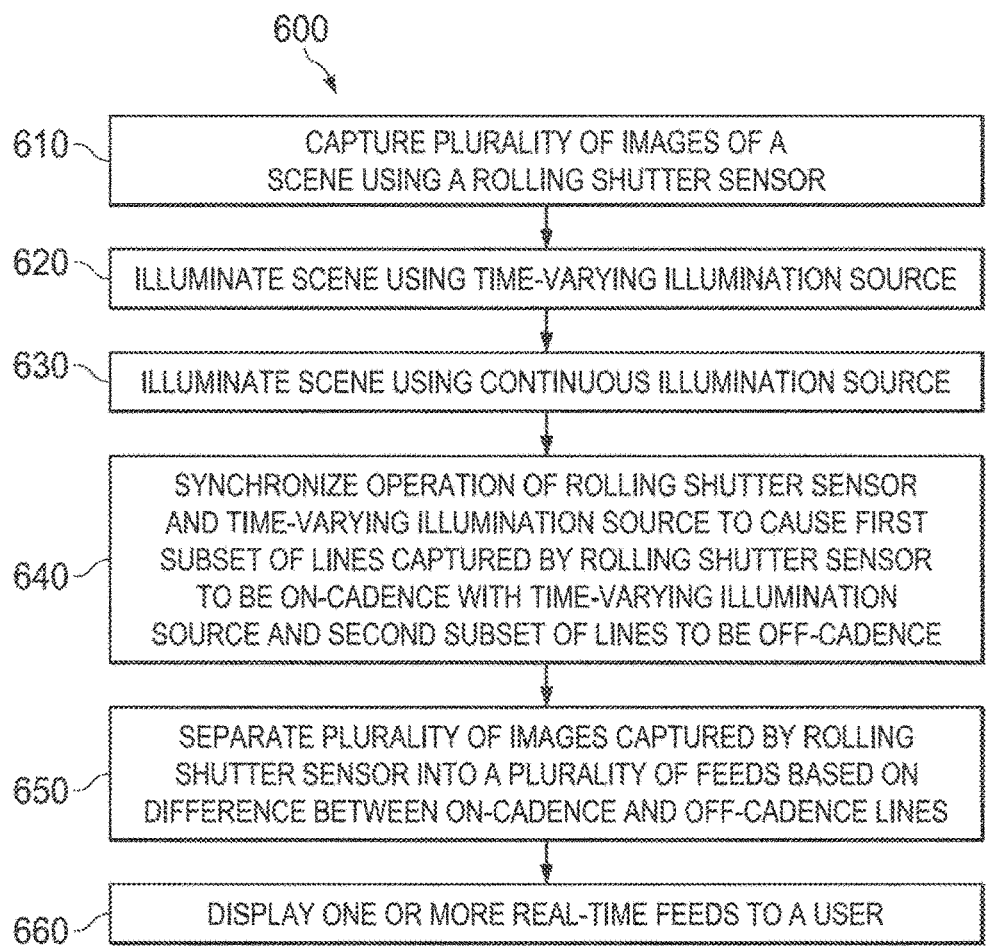
FIG. 6 is a simplified diagram of a method for extracting multiple image or video feeds from a rolling shutter sensor according to some embodiments.

FIG. 6 is a simplified diagram of a method 600 for extracting multiple image or video feeds from a rolling shutter sensor according to some embodiments. According to some embodiments consistent with FIGS. 1-5, method 600 may be performed during the operation of an imaging system, such as imaging system 400.

At a process 610, a plurality of images of a scene, such as scene 415, is captured using a rolling shutter sensor, such as rolling shutter sensor 410. The plurality of images are captured at a frame rate of the rolling shutter sensor. Each frame or image in the plurality of images is captured by scanning the scene line by line (e.g., vertically or horizontally) at a line rate of the rolling shutter sensor. As discussed previously with respect to FIG. 4, the rolling shutter sensor may be a CMOS imager incorporated into a chip-on-tip endoscope.

At a process 620, the scene is illuminated using a time-varying or time-varying illumination source, such as time-varying illumination source 420. According to some embodiments, the time-varying illumination source may be a fluorescence illumination source that causes objects or features in the scene that are labeled with fluorescent tags to fluoresce. According to some embodiments, the time-varying illumination source may be a structured illumination source that outputs a pattern (e.g., a dot, stripe, or grid pattern) used for optical ranging and/or depth estimation. The time-varying illumination source is operated at a pulse rate that is much greater than the frame rate of the rolling shutter sensor, as discussed previously with respect to FIG. 4.

At an optional process 630, the scene is illuminated using a continuous illumination source, such as continuous illumination source 430. For example, the continuous illumination source may be a white light source that enhances the overall visibility of objects in the scene. In some examples, process 630 may be omitted, such as when the scene is illuminated by ambient light.

At a process 640, the operation of the rolling shutter sensor and the time-varying illumination source is synchronized to cause a first subset of lines captured by the rolling shutter sensor to be on-cadence with the time-varying illumination source and a second subset of lines to be off-cadence. The on-cadence lines receive more illumination from the time-varying illumination source than the off-cadence lines. In some examples, consecutive lines in a given frame or image may alternate between on-cadence and off-cadence. Similarly, a given line may alternate between on-cadence and off-cadence in consecutive frames. For example, as depicted in FIG. 5, odd and even lines are on-cadence and off-cadence, respectively, in the first frame. Meanwhile, the opposite is true in the second frame: odd lines are off-cadence and even lines are on-cadence. The particular ratio between the amount of illumination captured in the on-cadence lines versus the off-cadence lines depends on the relationship between the line rate of the rolling shutter sensor, the modulation frequency (e.g., the pulse rate) of the time-varying illumination source, and the shutter size. For examples, when the pulse rate is half the line rate and the shutter size is three lines (i.e., the configuration illustrated in FIG. 5), the on-cadence lines receive twice as much illumination from the time-varying illumination source as the off-cadence lines.

At a process 650, the plurality of images captured by the rolling shutter sensor is separated into a plurality of image or video feeds based on the difference between the on-cadence and off-cadence lines. For example, when a given line alternates between on-cadence and off-cadence in consecutive frames, a line from the first frame may be compared pixel-by-pixel to the same line in the next frame to determine the pixel by pixel difference. In each of the plurality of video feeds, the contribution of the time-varying illumination source to the overall illumination of the scene is different. In some embodiments, the contribution of the time-varying illumination source may be removed from a first or general-purpose video feed and the contribution of the time-varying illumination source may be isolated in a second or special-purpose video feed. For example, the general-purpose video feed may correspond to the scene as illuminated by an ambient light source and/or the continuous illumination source of process 630. A first special-purpose video feed may correspond to fluorescence imaging that allows for a visualization of objects or features that are labeled using fluorescent tags. A second special-purpose video feed may correspond to structured illumination that allows for the depth of objects or features to be estimated. In some example, more than one fluorescent agent may be used, in which case one or more additional special-purpose video feeds may be separated at process 650.

At an optional process 660, one or more real-time image or video feeds are displayed to a user, such as Surgeon 20, via a display, such as surgeon console 10 and/or display 460. In some examples, the general-purpose video feed and the special-purpose video feed may be concurrently displayed to the user. For example, in endoscopy applications, the general-purpose video feed may be used for navigational purposes to guide the endoscope through the patient anatomy, while the special-purpose video feed may be used for clinical purposes such as to identify anatomical features that are labeled using fluorescent tags. Advantageously, each of the video feeds are captured concurrently and displayed in real-time, which eliminates a step of manually switching between the general-purpose video feed and the special-purpose video feed. In some embodiments, a single video feed may be displayed that combines information from the general-purpose video feed and the special-purpose video feed so as to enhance the amount of information conveyed to the operator within the single video feed. For example, the combined video feed may show images in which the special purpose video feed (e.g., fluorescent video) is overlaid on the general-purpose video feed. In some examples, the single video feed may display three-dimensional image data that combines two dimensional images from the general-purpose video feed with depth information extracted from the special-purpose video feed.

Figure 7:
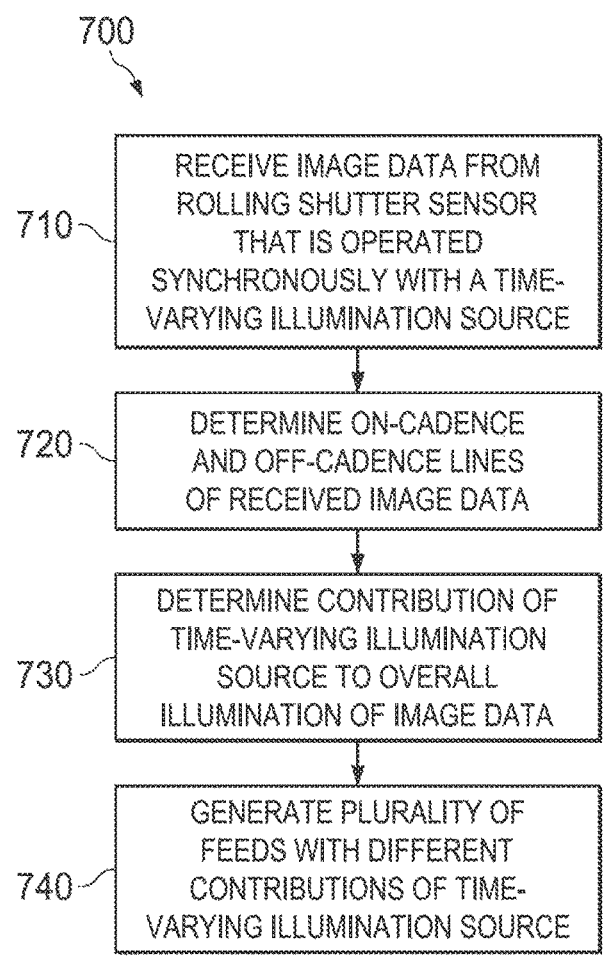
FIG. 7 is a simplified diagram of a method for separating image data into a plurality of image or video feeds according to some embodiments.

FIG. 7 is a simplified diagram of a method 700 for separating image data into a plurality of image or video feeds according to some embodiments. According to some embodiments consistent with FIGS. 1-6, method 700 may be carried out by a processor of an imaging system, such as processor 450 and/or 540. In some examples, method 700 may be used to implement one or more processes of method 600, such as process 650.

At a process 710, image data is received from a rolling shutter sensor, such as rolling-shutter sensor 410, that is operated synchronously with a time-varying illumination source, such as time-varying illumination source 420. The image data corresponds to a plurality of frames captured by the rolling shutter sensor. For example, the image data may be captured using a process corresponding to processes 610-640 as described above.

At a process 720, on-cadence and off-cadence lines of the received image data are determined. The on-cadence lines are those lines that are timed to receive more illumination from the time-varying illumination source than the off-cadence lines. In some examples, consecutive lines in a given frame may alternate between on-cadence and off-cadence. In some examples, a given line may alternate between on-cadence and off-cadence in consecutive frames. The determination of which lines are on- and off-cadence may include receiving a timing signal from the rolling shutter sensor, the pulsed light source, and/or a synchronization module responsible for synchronizing the operation of the rolling shutter sensor and the pulsed light source. Based on the timing signal, on-cadence and off-cadence lines may be identified. In some examples, on-cadence and off-cadence lines may be determined based on a priori knowledge of the relationship between the line rate of the rolling shutter sensor and the pulse rate of the time-varying illumination source.

At a process 730, a contribution of the time-varying illumination source to the overall illumination in the image data is determined based on a difference between the on-cadence and off-cadence lines. In some embodiments, for each line of the rolling shutter sensor, a pixel-by-pixel intensity difference between an on-cadence version of a line from one frame and an off-cadence version of the same line from another frame is determined. For example, when a given line alternates between on-cadence and off-cadence in consecutive frames, the on-cadence version of the line and the off-cadence version of the line are taken from neighboring frames. The difference between versions may be determined by subtracting and/or dividing two version of the line. Based on this difference, the contribution (e.g., a ratio and/or an absolute measure of illumination intensity) of the time-varying illumination source to the overall illumination may At a process 740, a plurality of image or video feeds with different contributions of the time-varying illumination source are generated. For example, a general-purpose video feed may be generated by modifying the image data to remove the contribution of the time-varying illumination source. Similarly, a special-purpose video feed may be generated by isolating the contribution of the time-varying illumination source. For example, for a pair of consecutive frames, the special-purpose video feed may depict the differential intensity between the pair of frames, and the common-mode intensity may be removed.

Some examples of processors, such as processor 450 and/or 540 may include non-transient, tangible, machine readable media that include executable code that when run by one or more processors (e.g., processor 450 and/or 540) may cause the one or more processors to perform the processes of methods 600 and/or 700. Some common forms of machine readable media that may include the processes of methods 600 and/or 700 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An imaging system, comprising:
   a rolling shutter sensor that captures a plurality of images of a scene;
   a continuous illumination source that illuminates the scene;
   a time-varying illumination source that illuminates the scene; and
   a processor configured to:
      synchronize the rolling shutter sensor and the time-varying illumination source to cause a first subset of lines of the rolling shutter sensor to be on-cadence with the time-varying illumination source and a second subset of lines to be off-cadence; and
      separate the plurality of images into a plurality of feeds, wherein each of the plurality of feeds has a different contribution of the time-varying illumination source to an overall illumination of the scene, and wherein the plurality of feeds comprise a general-purpose feed from which the contribution of the time-varying illumination source to the overall illumination of the scene is removed and a special-purpose feed in which the contribution of the time-varying illumination source is isolated.

2. The imaging system of claim 1, wherein the processor is configured to concurrently display the plurality of feeds to a user in real-time.

3. The imaging system of claim 1, wherein the rolling shutter sensor is a complementary metal-oxide-semiconductor (CMOS) imager.

4. The imaging system of claim 1, wherein the rolling shutter sensor is integrated into a chip-on-tip endoscope.

5. The imaging system of claim 1, wherein the rolling shutter sensor is operated at a frame rate of 60 Hz and a line rate of 61.44 kHz.

6. The imaging system of claim 1, wherein illuminating the scene includes pulsing the time-varying illumination source to generate a stream of equally spaced pulses.

7. The imaging system of claim 1, wherein a modulation frequency of the time-varying illumination source is significantly higher than a frame rate of the rolling shutter sensor.

8. The imaging system of claim 1, wherein the time-varying illumination source is a solid state illumination source.

9. The imaging system of claim 1, wherein the processor is further configured to modulate the time-varying illumination source using a time-varying electrical power supply.

10. The imaging system of claim 1, wherein the time-varying illumination source is a mode-locked laser that has a repetition rate synchronized with a line rate of the rolling shutter sensor.

11. The imaging system of claim 1, wherein the time-varying illumination source is a source of narrowband illumination.

12. The imaging system of claim 1, wherein the time-varying illumination source is a fluorescence illumination source with a wavelength corresponding to an excitation spectrum of a fluorescent agent in the scene.

13. The imaging system of claim 1, wherein the time-varying illumination source is a structured illumination source.

14. The imaging system of claim 13, wherein the processor is further configured to perform depth estimation based on an illumination pattern output by the structured illumination source.

15. The imaging system of claim 1, wherein the processor is further configured to generate and transmit synchronized timing signals to each of the rolling shutter sensor and the time-varying illumination source.

16. An imaging system comprising:
   a time-varying illumination source that illuminates a scene;
   a rolling shutter sensor that captures image data, the rolling shutter sensor operated synchronously with the time-varying illumination source;
   a continuous illumination source that illuminates the scene; and
   a processor configured to:
      determine on-cadence lines and off-cadence lines from the captured image data;
      determine a contribution of the time-varying illumination source to an overall illumination in the image data; and
      generate a plurality of feeds with different contributions of the time-varying illumination source to the overall illumination, wherein the plurality of feeds comprise a general-purpose feed from which the contribution of the time-varying illumination source to the overall illumination of a scene is removed and a special-purpose feed in which the contribution of the time-varying illumination source is isolated.

17. The imaging system of claim 16, wherein the processor is further configured to concurrently display the plurality of feeds to a user in real-time.

18. The imaging system of claim 16, wherein the rolling shutter sensor is a complementary metal-oxide-semiconductor (CMOS) imager.

19. The imaging system of claim 16, wherein the rolling shutter sensor is integrated into a chip-on-tip endoscope.

20. The imaging system of claim 16, wherein the time-varying illumination source generates a stream of equally spaced illumination pulses.

21. The imaging system of claim 16, wherein a modulation frequency of the time-varying illumination source is significantly higher than a frame rate of the rolling shutter sensor.

22. The imaging system of claim 16, wherein the time-varying illumination source is a solid state illumination source.

23. The imaging system of claim 16, wherein the time-varying illumination source is a mode-locked laser that has a repetition rate synchronized with a line rate of the rolling shutter sensor.

24. The imaging system of claim 16, wherein the time-varying illumination source is a source of narrowband illumination.

25. The imaging system of claim 16, wherein the time-varying illumination source is a fluorescence illumination source with a wavelength corresponding to an excitation spectrum of a fluorescent agent in a scene.

26. The imaging system of claim 16, wherein the time-varying illumination source is a structured illumination source.

27. The imaging system of claim 26, wherein the processor is further configured to perform depth estimation based on an illumination pattern output by the structured illumination source.

28. The imaging system of claim 16, wherein the processor is further configured to generate and transmit synchronized timing signals to each of the rolling shutter sensor and the time-varying illumination source.

* * * * *